United States Patent [19]

Adair

[11] Patent Number: 5,329,940

[45] Date of Patent: Jul. 19, 1994

[54] ENDOTRACHEAL TUBE INTUBATION ASSIST DEVICE

[76] Inventor: Edwin L. Adair, 2800 S. University Blvd., Denver, Colo. 80210

[21] Appl. No.: 821,788

[22] Filed: Jan. 16, 1992

Related U.S. Application Data

[63] Continuation of Ser. No. 479,833, Feb. 14, 1990, abandoned.

[51] Int. Cl.⁵ .......................................... A61M 16/00
[52] U.S. Cl. .......................... 128/200.26; 128/207.14
[58] Field of Search ............ 128/6, 11, 207.14, 207.15, 128/200.26

[56] References Cited

U.S. PATENT DOCUMENTS

| | | | |
|---|---|---|---|
| 3,677,262 | 7/1972 | Zukowski | 128/6 |
| 3,776,222 | 12/1973 | Smiddy | 128/6 |
| 4,427,000 | 1/1984 | Ueda | 128/6 |
| 4,688,554 | 8/1987 | Habib | 128/4 |
| 4,714,075 | 12/1987 | Krauter | 128/4 |
| 4,736,733 | 4/1988 | Adair | 128/6 |
| 4,754,328 | 6/1988 | Barath | 358/98 |
| 4,755,873 | 7/1988 | Kobayashi | 358/98 |
| 4,758,222 | 7/1988 | McCoy | 604/95 |
| 4,782,819 | 11/1988 | Adair | 128/6 |
| 4,846,153 | 7/1989 | Berci | 128/6 |
| 4,905,669 | 3/1990 | Bullard et al. | 128/11 |
| 4,947,896 | 8/1990 | Bartlett | 128/11 |
| 4,949,716 | 8/1990 | Chenoweth | 128/207.14 |
| 4,982,729 | 1/1991 | Wu | 128/11 |

Primary Examiner—Edgar S. Burr
Assistant Examiner—Aaron J. Lewis
Attorney, Agent, or Firm—Fields, Lewis, Pittenger & Rost

[57] ABSTRACT

An endotracheal tube intubation assist device in which an endoscope is utilized to provide a visual image as an aid in performing the intubation of an endotracheal tube within a patient's trachea. The assist device includes a handle, a malleable elongated insertion section and an endoscope assembly having a viewing end mounted within the insertion section to provide a visual image of the trachea. In use, the endotracheal tube is placed around the insertion section and removably attached to the handle for insertion into the trachea. The malleable insertion section can be bent by the attending medical personnel for providing a custom fit for the patient at hand. The handle of the assist device is also formed with an oxygen supply conduit for supplying oxygen to the patient during the intubation process. Additionally, the handle includes a suction port for attaching a suction tube for evacuation of the trachea during the intubation process.

3 Claims, 3 Drawing Sheets

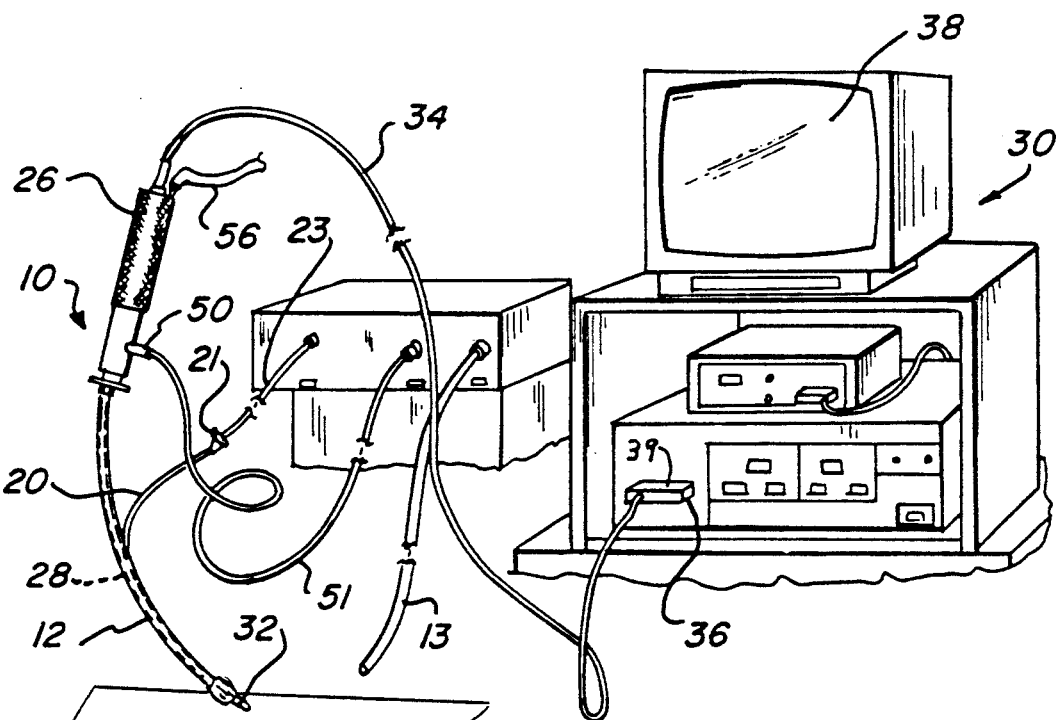
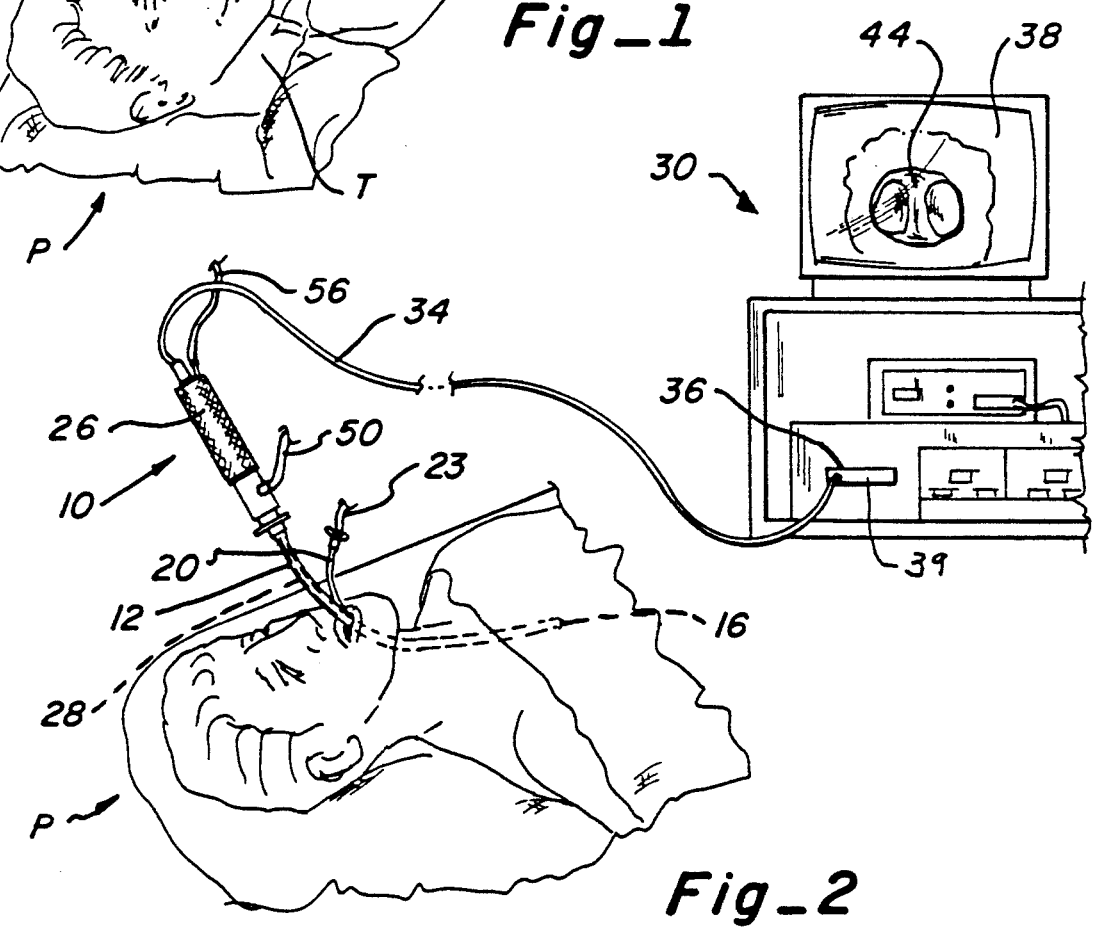
Fig_1
Fig_2

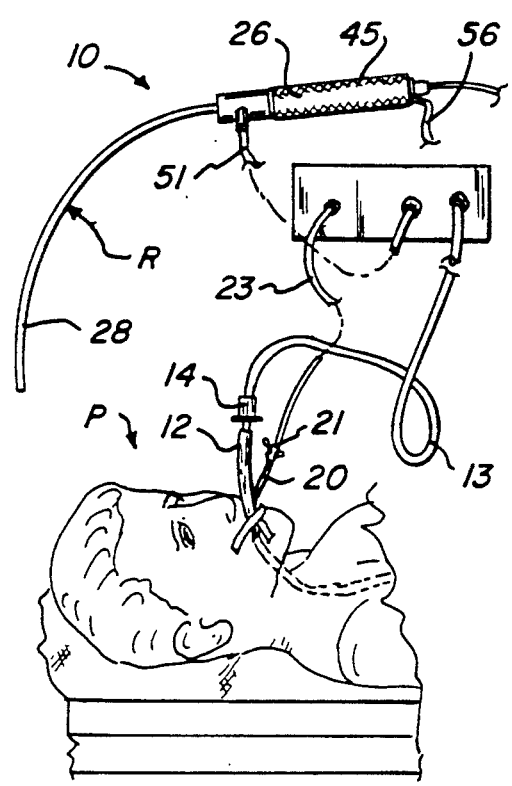
Fig_3
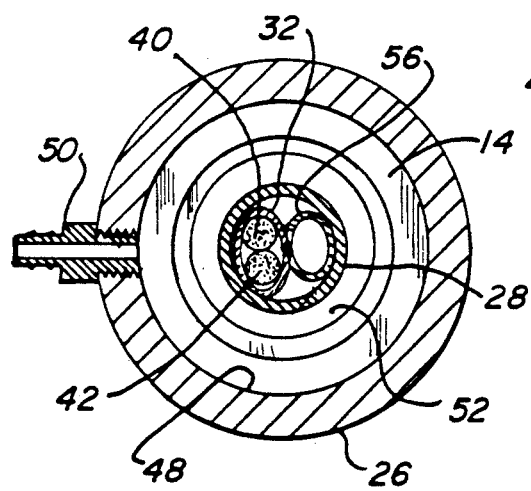
Fig_7
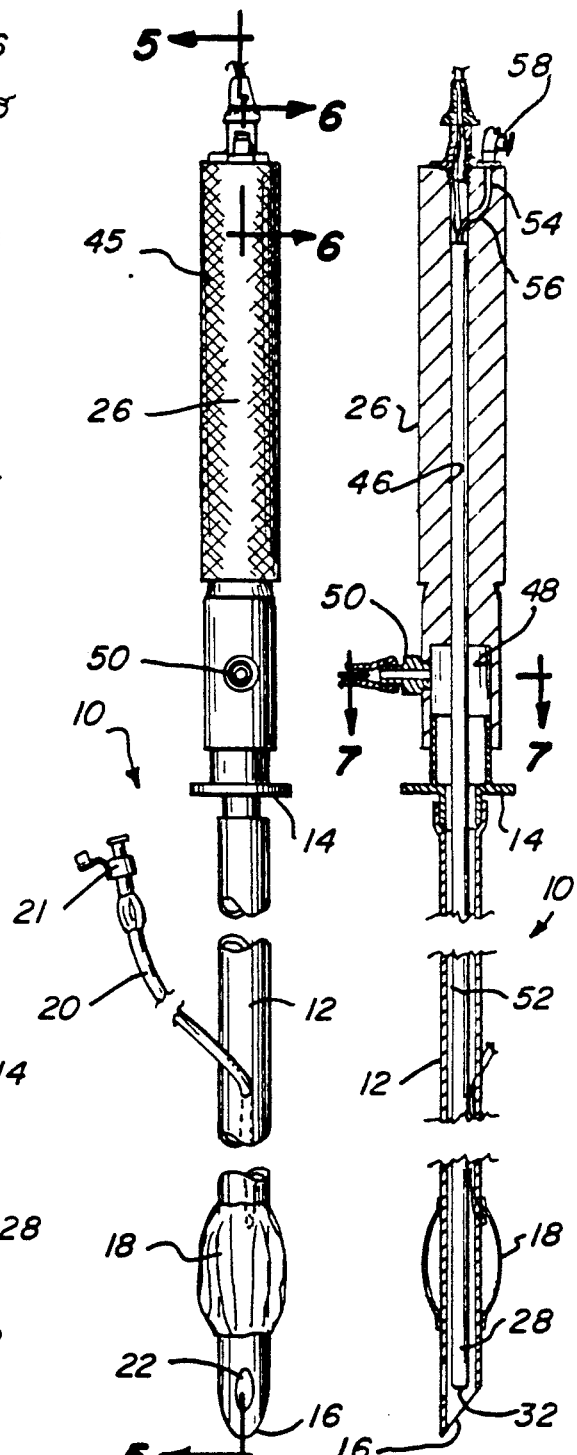
Fig_4  Fig_5

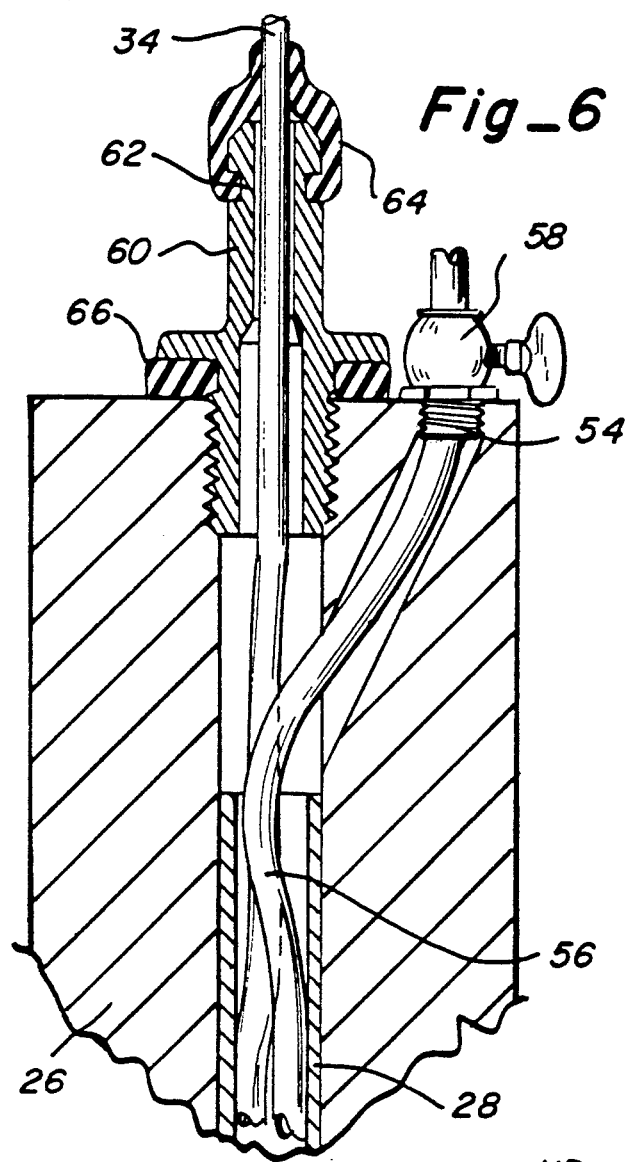
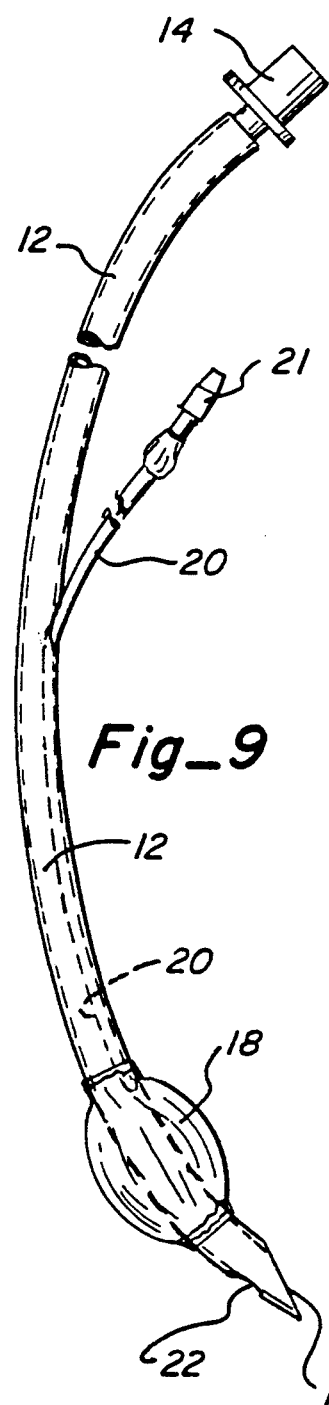
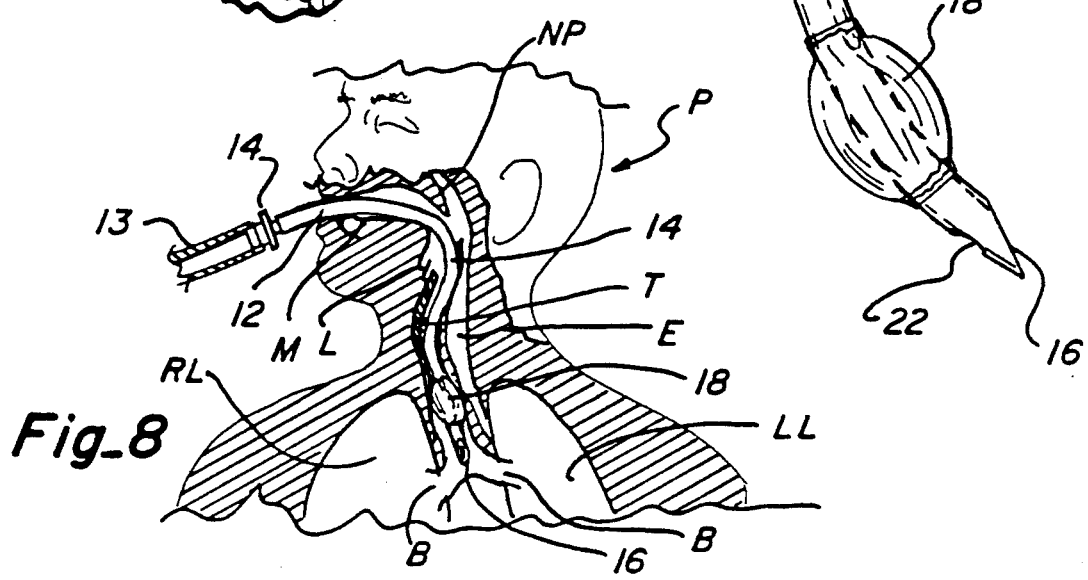

ENDOTRACHEAL TUBE INTUBATION ASSIST DEVICE

This is a continuation of U.S. application Ser. No. 07/479,833 filed Feb. 14, 1990, now abandoned.

TECHNICAL FIELD

This invention relates to endotracheal tubes and more particularly to an endotracheal tube intubation assist device wherein a fiber optic endoscope is utilized to provide a visual image of the interior of the trachea as an aid in manipulating the assist device for performing the insertion of an endotracheal tube.

BACKGROUND ART

Fiber optic endoscopes are utilized in a variety of medical procedures. In general, a fiber optic endoscope is an instrument which can be inserted into a body cavity to provide a remote image of the body cavity. An endoscope typically includes an insertion section and an external control section. The insertion section is adapted to be inserted into a body cavity. The insertion section typically includes a light carrying bundle of optical fibers, an optical objective lens and a fiber optic coherent cable which carries an optical image to the control section. The control section includes a light source and processing means for processing the image received from the optical bundle. The control section also includes displaying means, such as an eyepiece or television monitor, for displaying a visual image of the body cavity. U.S. Pat. No. 4,754,328 to Barath is representative of these type of endoscopes.

In some types of endoscopes, the insertion section of the endoscope can be shaped or bent in a controlled manner by external manipulation to guide the endoscope through a body cavity. This allows the insertion section to be maneuvered through the body cavity without causing harm to the patient. These types of endoscopes are typically utilized for examination of the digestive tract. U.S. Pat. No. 4,688,554 to Habib, U.S. Pat. No. 4,755,873 to Kobayaski, and U.S. Pat. No. 4,714,075 to Krauter, are representative of these types of endoscopes.

One area of medicine in which an endoscope has heretofore not been generally utilized, is in the insertion of an endotracheal tube within the trachea of a patient. This is a common medical procedure in which an endotracheal tube is located within the trachea and then connected to a supply conduit to supply oxygen or anesthetic gases to the lungs. Prior to insertion of the endotracheal tube, the trachea must often be evacuated to clear mucous, blood, or other debris from the trachea.

In some cases, endotracheal intubation may be difficult to accomplish. This may be due to the fact that the patient is severely injured or because different patients, depending on their body size, age, and sex have differently shaped pathways into the trachea. The intubation process if incorrectly done may cause injuries to the patient, such as tears and damage to the larynx, trachea, nasopharynx and bronchi. Additionally, improper placement of the endotracheal tube, such as in the esophagus, (swallowing tube leading to the stomach) or in only one bronchus, (left or right) of the lung, may provide serious complications for a patient.

It is apparent then that an external visual image of the trachea would be helpful for use in this medical intubation process. In other cases such as in the training of medical personnel or when used by relatively inexperienced medical personnel, an external visual image of the trachea would also be quite helpful in the intubation process.

DISCLOSURE OF THE INVENTION

Accordingly, this invention relates to an assist device for performing an endotracheal tube intubation in a medical patient, in which an endoscope is utilized to provide a visual image as an aid in the insertion and intubation process. Additionally, the assist device is constructed with a malleable insertion section which may be bent to a shape which is most accommodating to a particular patient.

The endotracheal intubation assist device of the invention, generally stated, comprises, a handle, a malleable metal insertion section attached to the handle, and an endoscope having a viewing end mounted within the insertion section to provide a visual image of the trachea and related body structures while the intubation is being accomplished.

In general, an endotracheal tube is a breathing conduit formed of a soft flexible plastic medical tubing material adapted to be placed into a patient's trachea. The endotracheal tube is open at a distal end where oxygen or other gases are directed into the lungs. The proximate end of the endotracheal tube is typically formed with a tube fitting adapted to be connected to a source of pressurized gas such as oxygen or gases for anesthesia. The endotracheal tube may also include an inflatable bladder or balloon at a distal end which can be inflated by air pressure to contact the trachea and seal the endotracheal tube within the trachea just above the bronchi of the lungs. In use, an endotracheal tube must be centered between the two opposite bronchi (right and left) of the lungs and sealed within the trachea such that the lungs are equally supplied by gas flow through the open distal end of the endotracheal tube into the bronchi.

During the intubation process the flexible endotracheal tube must be traversed through the mouth, the nasopharynx, the larynx and the trachea of the patient and placed in a proper position within the trachea without causing damage to any body structures. The assist device of the invention functions as an aid in effecting this intubation process.

The handle and insertion section of the assist device are constructed such that a standard endotracheal tube may be placed around the insertion section and attached to the handle. The insertion section is formed of a malleable material such as malleable stainless steel or silver tubing and may be bent by an operator to accommodate the shape of the trachea of the patient at hand. It is contemplated that different insertion sections may be sized for use with the different standard sizes of endotracheal tubes used for adults, children, or for smaller or larger people. The assist device may thus be customized by an operator to suit a particular patient.

As previously stated, the viewing end of the endoscope is mounted within the insertion section and provides a visual image of the trachea during the intubation process. In use, the handle can be manipulated using this visual image for guiding the insertion section and endotracheal tube into the trachea.

The endoscope of the assist device includes a viewing end with an optic objective lens and a light carrying bundle of optical fibers located at the open distal end of the insertion tube. The endoscope assembly also includes an external control section. A detachable cable unit having fiber optic cables passed through the insertion section and the handle of the assist device connect the viewing end of the endoscope to the external control section of the endoscope. The external control section includes a light source and processing means including a video camera for processing the image from the viewing end to produce a wide angle image of the body interior on a television monitor.

The external control section also includes a receptical on a front panel for receiving the cable unit. At the receptical an image bundle is precisely aligned to the optics and video camera inside the control unit. This receptical also precisely aligns the light carrying fibers in the cable unit to the light soure within the control unit.

The handle of the assist device is formed with an inner passageway wherein the insertion section is mounted. The handle may also include an oxygen supply conduit for providing oxygen to the patient during the intubation process. Additionally, a separate evacuation port is provided on the handle for passing a suction tube to aid in removing mucous, blood or other debris from the trachea during the intubation process.

In use of the assist device of the invention, a standard endotracheal tube suited to a particular patient is removably attached to the handle of the assist device placed around the malleable insertion section of the assist device. The malleable insertion section may be bent by hand by the physician or attending medical personnel to a shape that is most suited for maneuvering the insertion section and endotracheal tube through that particular patient's trachea.

The insertion section with the endotracheal tube attached may thus be guided by manipulation of the handle of the assist device into the patient's mouth, across the nasopharynx, larynx, and trachea of the patient, and positioned with the open end of the endotracheal tube located in the trachea between the bronchi of the lungs. During the intubation procedure the oxygen supply conduit attached to the handle of the assist device may temporarily supply oxygen to the lungs. Additionally evacuation of the mouth and tracheal area may also be accomplished by placing a suction tube through the suction port of the handle and into the trachea.

During the intubation process, an image of the body structure being traversed by the viewing end of the endoscope is transferred and shown on the monitor television. The handle of the assist device can be guided in response to this image to place the endotracheal tube in a proper position within the trachea.

Once the endotracheal tube is properly situated within the trachea between the bronchi of the lungs, the endotracheal tube may be disconnected from the handle and the insertion section may be removed from the endotracheal tube. The sealing bladder of the endotracheal tube may then be inflated and the endotracheal tube may be connected to a pressurized gas source such as oxygen or anesthetic gases.

From the foregoing, the advantages of this invention will become readily apparent, when taken in conjunction with the description of the drawing which follows.

BRIEF DESCRIPTION OF THE DRAWING

FIG. 1 is a perspective view of an endotracheal tube intubation assist device constructed in accordance with the invention and shown prior to intubation of an endotracheal tube into the trachea of a reclining patient;

FIG. 2 is a perspective view of the endotracheal tube intubation assist device shown during the intubation process;

FIG. 3 is a perspective view of the endotracheal tube intubation assist device shown after intubation of the patient has been completed and an inflatable bladder of the endotracheal tube is being inflated to seal the endotracheal tube within the patient's trachea;

FIG. 4 is a side elevation view of the endotracheal tube intubation assist device of the invention shown with an endotracheal tube attached;

FIG. 5 is a vertical cross section taken along section line 5—5 of FIG. 4 showing details of the internal structure of the endotracheal tube intubation assist device;

FIG. 6 is a partial enlarged vertical cross section taken along section line 6—6 of FIG. 4 showing details of the internal structure of the handle of the endotracheal tube intubation assist device of the invention;

FIG. 7 is a horizontal cross section taken along section line 7—7 of FIG. 5;

FIG. 8 is a perspective view partially cut away of a patient showing the final placement of the endotracheal tube in the patient; and FIG. 9 is a side elevation view of an endotracheal tube.

BEST MODE FOR CARRYING OUT THE INVENTION

Referring now to FIGS. 1-9, an endotracheal tube intubation assist device 10 constructed in accordance with the invention is shown for use with a medical patient P. The endotracheal tube intubation assist device 10 is intended for use in inserting and positioning an endotracheal tube 12 within the trachea T of the patient P.

As shown in FIG. 9, the endotracheal tube 12 is an elongated flexible plastic tube adapted to be inserted into the trachea T of the patient P and connected to an oxygen supply conduit 13 or the like (FIG. 3) for providing oxygen or other gases such as anesthetic gases to the patient P. The endotracheal tube 12 may be of a standard size and configuration and may include a tube fitting 14 at a proximate end which may be connected to the oxygen supply conduit 13 commonly found in hospitals and ambulances. The endotracheal tube 12 is open at a distal end 16 where the oxygen or other gases flow into the trachea T.

The endotracheal tube 12 may also include an inflatable bladder portion 18 which may be inflated for sealing the endotracheal tube 12 within the trachea T. The bladder portion 18 is connected to a compressed air conduit 20 having a standard tube fitting 21 at an exterior proximate end. This tube fitting 21 may be removably connected to a source of compressed air 23 (FIG. 3) or to an air pump for inflating the bladder portion 18. The inflated bladder 18 contacts the walls of the trachea T and seals the endotracheal tube 12 within the trachea T between the bronchi B (FIG. 8) of the lungs RL, LL of the patient P.

As shown in FIG. 8, the endotracheal tube 12 is intended to be inserted into the trachea T of a patient situated with its open distal end 16 located between the bronchi B of the lungs RL, LL to supply oxygen equally to the lungs RL, LL. In this position, the inflatable bladder 18 of the endotracheal tube 12 is inflated to press against the inner wall of the trachea T and seal the endotracheal tube 12 within the trachea T.

In positioning the endotracheal tube 12 within the trachea T, the endotracheal tube 12 must be maneuvered through the mouth M, nasopharynx NP, the larynx L, and the trachea T of the patient in that order. While the endotracheal tube 12 is being inserted into the trachea T care must be taken to avoid intubation of the endotracheal tube 12 in the esophagus E (swallowing tube leading to the stomach). Additionally, care must be taken to lodge the distal end 16 of the endotracheal tube 12 between the lungs RL, LL and not in a single bronchus B.

The endotracheal tube 12 is formed of a soft plastic material and as shown in FIG. 9, the distal end 16 of the endotracheal tube 12 is angled to aid in the passage of the endotracheal tube 12 through the trachea T. Additionally, the endotracheal tube 12 is formed with an opening 22 at its distal end 16 which aids in the equal dispersion of oxygen into the lungs LL, RL.

Referring now to FIGS. 1-4, the endotracheal tube intubation assist device 10 of the invention is shown. The endotracheal tube intubation assist device 10 generally stated comprises, a handle portion 26, an insertion section 28, and an endoscope assembly 30 having a viewing end 32 mounted within the insertion section 28 to provide an image of the mouth, nasopharynx, larynx and trachea as the endotracheal tube 12 is passed therethrough. The handle portion 26 of the assist device 10 includes attachment means for attaching the insertion section 28 and endotracheal tube 12.

As shown in FIG. 1, the endoscope assembly 30 includes the viewing end 32 (FIG. 5) mounted within the insertion section 28 of the assist device 10, and an external control section. An optic cable assembly 34 connects the control section to the viewing end 32. The optic cable assembly 34 includes a plurality of fiber optic bundles. A light carrying bundle provides a pathway from a light source to the viewing end 32. An image carrying bundle provides a pathway for an image from the viewing end 32 to the external control section of the endoscope assembly 30. The control section includes a processing unit 36 for processing the image from the viewing end 32, and a TV monitor 38 for presenting a wide angle visual image 44 of the body interior for the operator of the assist device 10.

In general the processing unit 36 of the control section allows the image picked up by a coherent fiber optic bundle at the viewing end 32 (FIG. 5) of the endoscope assembly 30 to be innerfaced with optics which in turn deliver the image to a video camera (not shown). The video camera inside the processing unit 36 then delivers this image information electronically to the TV monitor 38.

Inside the optic cable assembly 34 are optic fibers which carry light from a light source (not shown) located inside the control unit. The light source delivers light to the fiber optic cable assembly 34 through a connector 39.

In general, connector 39 is a coupling which fits into a mating receptacle in a front panel of the control section of the endoscope assembly 30. This connector 39 functions to precisely aligns the image bundle to both optics and camera and precisely align the light carrying bundle to the light source.

The light source of the endoscope assembly 30 may be any high intensity light source such as xenon, mercury arc, halogen or laser light. In any case, the light source must be precisely aligned through the connector 39 to the light fibers in the optic cable assembly 34.

A light carrying bundle of optical fibers 40 (FIG. 7) terminate at the viewing end 32 of the endoscope assembly 30. This light carrying bundle of optical fibers 40 is connected to the light source within the control section 30 to provide illumination of the body cavity. Additionally the viewing end 32 includes an objective optic lens (FIG. 7) connected through the image carrying bundle 42 of the optic cable assembly 34 to the video camera of the control section 30.

The previously cited U.S. Pat. No. 4,754,328 to Barath and U.S. Pat. No. 4,782,819 to Adair disclose endoscope assemblies which include the above described components.

As shown in FIG. 2, this endoscope assembly 30 arrangement produces a wide angle visual image 44, of the interior of the body on the TV monitor 38. In use of the assist device 10, the operator of the assist device 10 such as a physician or other attending medical personnel, may use this wide angle visual image 44 in guiding and properly placing the endotracheal tube 12 within the trachea T.

With the present endoscope assembly 30, the eyepiece of a standard endoscope has been eliminated so that the medical personnel can work from a television monitor 38. This eliminates the use of an eyepiece and makes the intubation procedure much easier for the operator (no bending over). Also, other assistants can also see at the same time and better aid in the procedure.

Referring now to FIGS. 4-7 the construction of the handle 26 of the intubation assist device 10 is shown. The handle 26 is generally hollow and cylindrical in shape with an inner diameter and an outer diameter. The handle 26 includes a knurled outer surface 45 to provide a non-slip grip for the operator of the assist device 10. The handle 26 may be fabricated from a corrosion resistant metal or plastic material which is durable and easy to clean. By way of example only and not by limitation, the handle 26 may be sized (i.e. 1" o.d.×¼" i.d.×6" long) to be easily hand manipulated by an operator.

The handle 26 also includes an interior passageway 46 (FIG. 5) therethrough which functions as an attachment means for attaching the insertion section 28 of the assist device 10 to the handle 26. This attachment is accomplished by an interference fit between the mating components (i.d. of passageway 46 and o.d. of insertion section 28).

In addition and as shown in FIG. 5, the handle 26 includes a counterbore 48 at a lower end which functions as an attachment means for attaching the endotracheal tube 12 to the handle 26. This attachment is accomplished by placing the endotracheal tube 12 around or circumjacent to the insertion section 28 and pressing the tube fitting 14 on the proximate end of the endotracheal tube 12 into the counterbore 48 of the handle 26. Again, an interference fit between the mating elements (i.d. of counterbore 48, o.d. of fitting 14), attaches the mating elements to one another in air-tight relationship. Additionally, the tube fitting 14 of the endotracheal tube 12 may be tapered or angled to wedge into the counterbore 48.

With the endotracheal tube 12 attached to the handle 26 and as shown in FIG. 5, the insertion section 28 does not extend past the distal end 16 of the endotracheal tube 12. This insures that the hard external surface of the insertion section 28 does not contact the trachea or other body structures during the intubation process.

The handle 26 of the assist device 10 also includes a tube fitting 50 placed through the handle 26 and in communication with the counterbore 48 of the handle 26. In use of the assist device 10, an oxygen supply conduit 51 (FIG. 1) may be attached to the tube fitting 50 as an oxygen supply means for providing oxygen to the patient P during the intubation process. As is apparent from FIG. 5, oxygen can flow under pressure from the oxygen supply conduit 51 through the tube fitting 50, into the counterbore 48 of the handle 26, through tube fitting 14 of the endotracheal tube 12, and through an annular space 52 which is formed between the inside diameter of the circumferentially mounted endotracheal tube 12 and the outside diameter of the insertion section 28 of the assist device 10. During the intubation process, oxygen may thus flow out the open end 16 of the endotracheal tube 12 and into the trachea T of the patient P.

The handle 26 of the assist device 10 also includes a suction port 54 wherein a flexible suction tube 56 may be placed into the handle 26 through the inside diameter of the insertion section 28 and into the trachea T. The suction tube 56 may be utilized as an evacuation means to evacuate blood, mucous, and other debris from the trachea T prior to and during the intubation process. A control valve 58 attached to the handle 26, seals the suction port 54 when it is not in use. It should be understood that the oxygen delivery system and the suction system are "add-on" functions of the assist device 10 and are not essential to its operation. It is contemplated that devices will be available with and without these features.

With reference to FIG. 6, the handle 26 of the assist device 10 also includes a sealing coupling 60 having a male connector 62. The coupling 60 is attached to a proximate end of the handle 26 and provides means for opening the internal diameter 46 of the handle 26 for placing the viewing end 32 and optic cable assembly 34 through the handle 26 into the inner diameter of the insertion section 28. The optic cable assembly 34 includes a boot or female connector 64 which snaps onto the male connector 62 to seal the optic cable assembly 34. A seal member 66 seals the coupling 60 of the handle 26 to the handle 26.

In use of the assist device 10 of the invention, an endotracheal tube 12 sized for a particular patient P, is placed around or circumjacent to the outside diameter of the insertion section 28 of the assist device 10. The malleable insertion section 28 is also sized with a length which suits the patient P at hand. The malleable insertion section 28 is then bent by hand by the physician or other attending medical personnel to accommodate the patient P. As all example a suitable radius of curvature "r" is shown in FIG. 3.

In bending the malleable insertion section 28 to a shape that most easily passes through the trachea T of the patient P, the operator may utilize medical experience and training, and consider such factors as the size, age, sex, and medical condition of the patient P.

The insertion section 28 is preferably formed of a malleable material such as specially treated stainless steel tubing which can be easily bent to the required shape and will maintain this customized shape during the intubation process. Once the insertion section 28 has been bent to shape as required, the insertion section 28 can be attached to the interior passageway 46 of the handle 26. As previously explained, the inner diameter of the interior passageway 46 of the handle and the outside diameter of the insertion section 28 are accurately formed to provide a tight interference fit between the mating parts. The insertion section 28 thus becomes an extension of the handle 26 and the two elements become one. After the insertion section 28 has been attached to the handle 26, the endotracheal tube 12 can also be attached to the handle 26 by placing the endotracheal tube 12 around the insertion section 28 and by sliding tube fitting 14 of the endotracheal tube 12 into the counterbore 48 on the handle 26.

Prior to insertion of the insertion section 28 into the patient's mouth M, the oxygen supply conduit 51 can be attached to the tube fitting 50 on the handle 26. Additionally, the suction tube 56 can be passed through the handle 26 and into the internal diameter of the insertion section 28. This arrangement of the assist device 10 prior to insertion into the patient P is clearly shown in FIG. 1.

Next and as shown in FIG. 2, the insertion section 28 may be guided by the operator into the patient's mouth, through the nasopharynx, larynx, and trachea and situated with the open distal end of the endotracheal tube 12 positioned in the trachea above the bronchi B of the lungs RL, LL. This correct placement of the endotracheal tube 12 is clearly shown in FIG. 8.

In passing tile endotracheal tube 12 and insertion section 28 into the trachea T, a visual image 44 of the body interior is shown on the TV monitor 38. This visual image 44 is formed as the viewing end 44 of the endoscope assembly 30 passes through the trachea T. This visual image 44 allows the physician to manipulate the handle 26 and to guide the insertion section 28 into correct position within the trachea T, without causing ham to the patient.

During the intubation process, suction tube 56 situated at the distal end of the insertion section 28 provides evacuation of blood, mucous, and debris from the trachea T. In addition during this intubation process, oxygen may flow from the oxygen supply conduit 51 through the insertion section 28 and into the patient's trachea T to provide oxygen to the patient's lungs RL, LL.

Once the intubation has been completed and as shown in FIG. 3, tube fitting 14 at the proximate end of the endotracheal tube 12 can be removed from the handle 26. The handle 20 can then be manipulated to pull the insertion section 28 out of the patient's mouth. The endotracheal tube 12 can then be coupled to a source of compressed oxygen 13 for providing oxygen to the patient, or can be attached to a standard anesthesia machine for delivery of anesthetic gases.

Once the endotracheal tube 12 is properly placed within the trachea T, the inflatable bladder 18 of the endotracheal tube 12 can be inflated by air pressure from compressed air conduit 23. This seals the endotracheal tube 12 within the trachea T.

Thus the invention provides an assist device in which an endoscope can be utilized as an aid in performing an endotracheal tube intubation. Furthermore, the malleable insertion section of the assist device can be bent by the operator as required, to provide a custom fit for the patient at hand.

Although the invention has been described in detail with particular reference to a preferred embodiment thereof, it will be understood that variations and modifications can be effected within the spirit and scope of the invention.

What is claimed is:

1. An endotracheal tube and an intubation assist device for placing an endotracheal tube of predetermined length within a patient's trachea, said endotracheal tube having proximal and distal ends, said assist device including;

a substantially cylindrical handle having a central longitudinal axis, a proximate end and a distal end and having a centrally located single passageway extending longitudinally therethrough from one end to the other end along said axis;

a tubular insertion section, malleable along its entire length, having an open distal end and a proximate end received in said centrally located single passageway and extending through said cylindrical handle so that said centrally located single passageway and distal end of said tubular insertion section are in axial alignment, said distal end of said insertion section being positionable within the distal end of the endotracheal tube so that the entire length of said tubular insertion section is positionable within the endotracheal tube, and shapeable along its entire length to a substantially fixed configuration, prior to attachment of the endotracheal tube, for insertion into a patient without further manipulation;

attachment means at said distal end of said substantially cylindrical handle for removably attaching the endotracheal tube to said substantially cylindrical handle in air-tight relationship, with said insertion section removably positionable through the endotracheal tube but within the distal end thereof so that the endotracheal tube is formable to said predetermined substantially fixed configuration of said malleable insertion section and is in fixed relation thereto during insertion;

oxygen supply means extending through said substantially cylindrical handle for providing oxygen to the endotracheal tube during the intubation process; and an endoscope assembly having a viewing end located at the open distal end of said insertion section, locatable within the distal end of the endotracheal tube when it is connected to said attachment means, and including an optic lens, a light carrying bundle of optical fibers, processing means including a light source and a video camera for processing an image from the optic lens, an external viewing monitor for displaying a visual image from the viewing end, and an optic cable assembly placed through said insertion section to connect the light carrying bundle of optic fibers, optic lens and processing means; so that said insertion section and the endotracheal tube may be placed into the patient's trachea and said substantially cylindrical handle may be manipulated to insert the endotracheal tube within the trachea using a visual image within said distal end of said endotracheal tube as a guide.

2. The assist device as claimed in claim 1 and wherein:

said handle has an axial counterbore at said distal end thereof, said oxygen supply means extending into said counterbore; and said attachment means comprises a tube fitting having a distal end removably attachable to the endotracheal tube and a proximate end press fitted in airtight relationship into said counterbore in said handle.

3. An endotracheal tube and an intubation assist device for placing a flexible endotracheal tube having an open distal end and a proximate end, within a patient's trachea, said assist device comprising:

a generally cylindrical shaped handle formed with an outside diameter and a central longitudinal axis, said handle having a single central passageway therethrough which lies along said axis and having an axial counterbore at a distal end for receiving the proximate end of the endotracheal tube for attaching the endotracheal tube to the handle in fixed air-tight position during insertion;

an elongated insertion section or predetermined length having distal and proximate ends, formed along its entire length of a malleable tubing sized to be placed through the endotracheal tube and press fitted into the single central passageway of said handle so that the single central passageway and the elongated insertion section are in axial alignment, said distal end of said insertion section being positionable within the distal end of the endotracheal tube so that the entire length of the elongated insertion section is positionable within the endotracheal tube;

oxygen supply means extending through the side of said handle into said counterbore endotracheal tube during the intubation process; and an endoscope assembly having an objective optic lens and a light carrying bundle of optical fibers mounted at the open distal end of said insertion section, an optic cable assembly attached to the light carrying bundle of optical fibers and the optic lens, processing means attached to the optic cable assembly and including a light source connected to the light carrying bundle of optical fibers and a video camera for processing an image from the objective optic lens, and a TV monitor connected to the processing means for displaying a visual image so that said insertion section may be shaped by hand long its entire length to a predetermined substantially fixed configuration prior to attachment of said endotracheal tube for placement of the insertion section and conforming endotracheal tube within the patient's trachea using the visual image on the TV monitor of the end of the endotracheal tube as an aid for an operator in manipulating the handle to guide the endotracheal tube through the trachea.

* * * * *